United States Patent [19]

Wang et al.

[11] Patent Number: 5,192,416

[45] Date of Patent: Mar. 9, 1993

[54] METHOD AND APPARATUS FOR BATCH INJECTION ANALYSIS

[75] Inventors: Joseph Wang; Ziad H. Taha, both of Las Cruces, N. Mex.

[73] Assignee: New Mexico State University Technology Transfer Corporation, Las Cruces, N. Mex.

[21] Appl. No.: 682,907

[22] Filed: Apr. 9, 1991

[51] Int. Cl.[5] ............................................. G01N 27/26
[52] U.S. Cl. .................................. 204/409; 204/416; 204/433
[58] Field of Search ................ 436/52, 53; 204/409, 204/412, 416, 433, 153.21, 153.1, 400

[56] References Cited

U.S. PATENT DOCUMENTS

| | | | |
|---|---|---|---|
| 4,003,705 | 1/1977 | Buzza et al. | 204/433 |
| 4,661,210 | 4/1987 | Tenygl | 204/153.1 |
| 4,695,555 | 9/1987 | O'Keeffe | 436/150 |
| 4,804,443 | 2/1989 | Newman et al. | 204/409 |
| 4,865,992 | 9/1989 | Hach et al. | 436/51 |
| 5,019,515 | 5/1991 | Gisin et al. | 436/55 |

FOREIGN PATENT DOCUMENTS

WO8909388 5/1989 PCT Int'l Appl. .

OTHER PUBLICATIONS

Stewart, "Flow Injection Analysis—New Tool for Old Assays—New Approach to Analytical Measurements" *Analytical Chemistry*, vol. 55, No. 9 (Aug. 1983).

*Primary Examiner*—John Niebling
*Assistant Examiner*—Bruce F. Beu
*Attorney, Agent, or Firm*—Deborah A. Peacock; Donovan F. Duggan; Rod D. Baker

[57] ABSTRACT

Batch injection analysis comprises apparatus and method for injecting and transporting analytes toward a detector immersed in a confined, inert electrolyte. Passage of the analyte over the detector surface provides measurement of sample concentrations. Detectors normally comprise selective electrodes, such as biologically or chemically modified surfaces, ion-selective probes, optical or thermal devices, thus eliminating conduits, valves, and pumps.

38 Claims, 19 Drawing Sheets

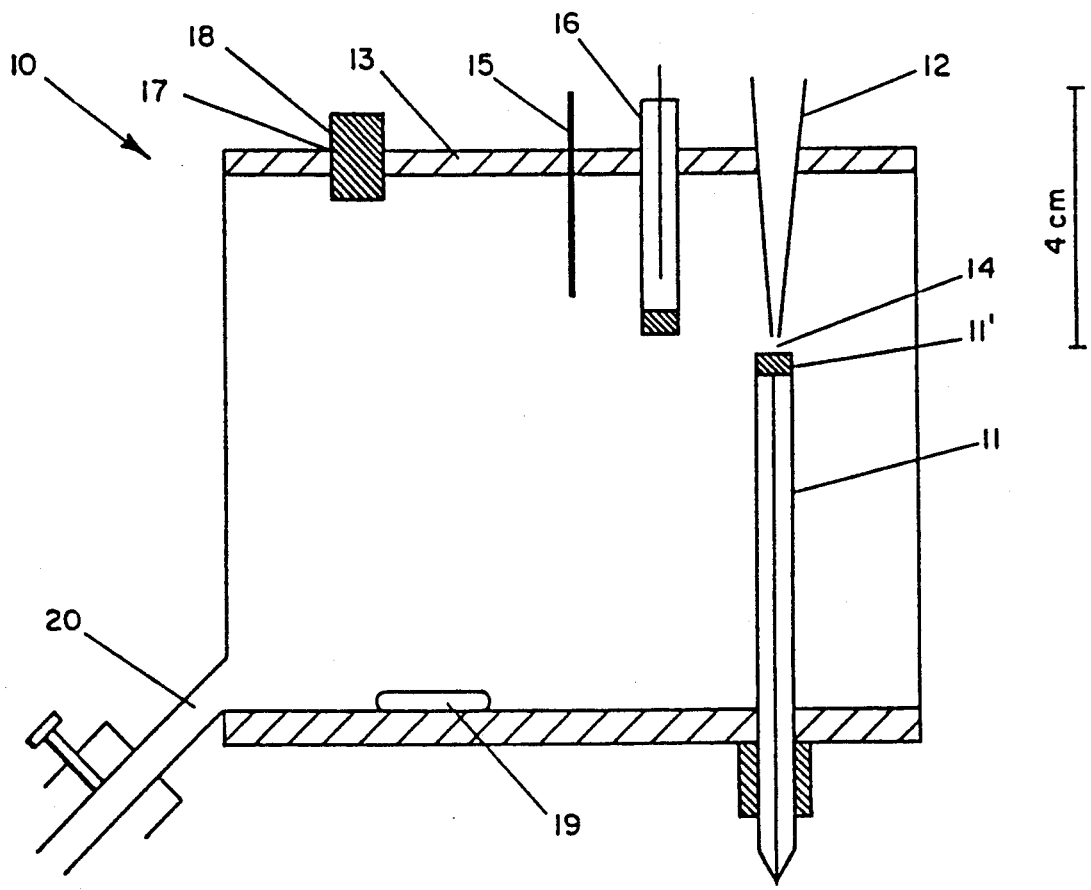
FIG—1
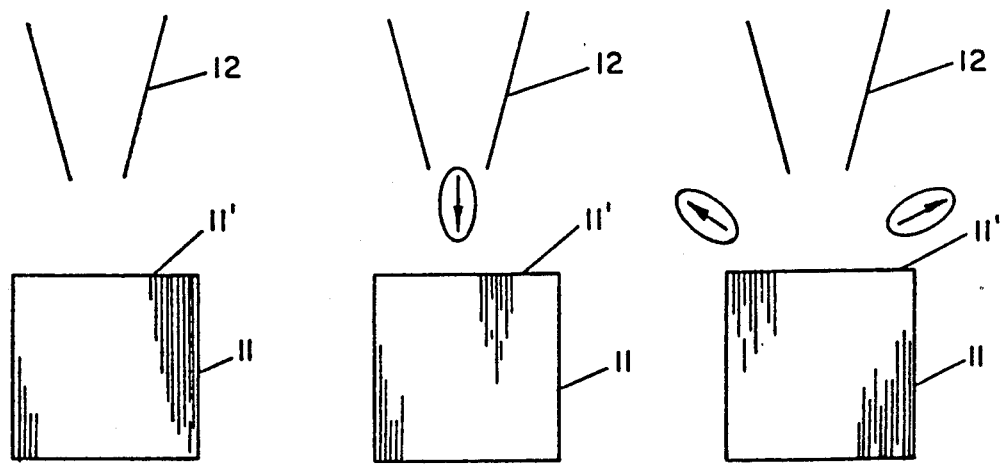
FIG—2a  FIG—2b  FIG—2c

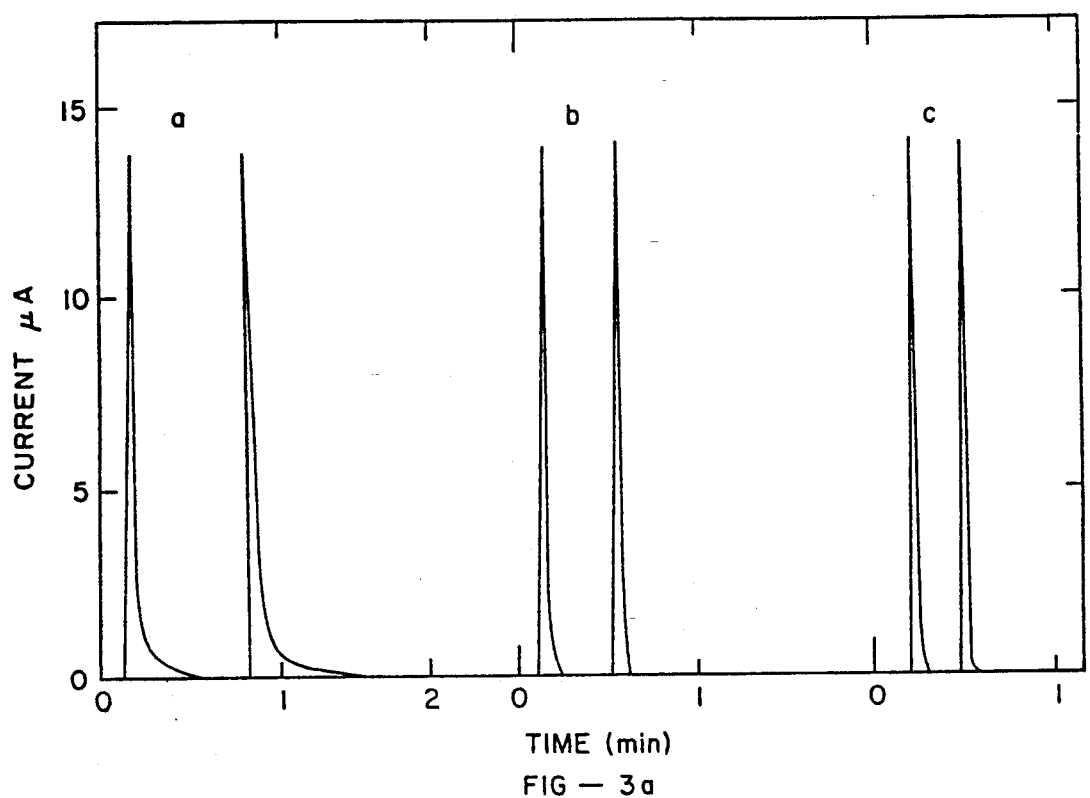
FIG — 3a
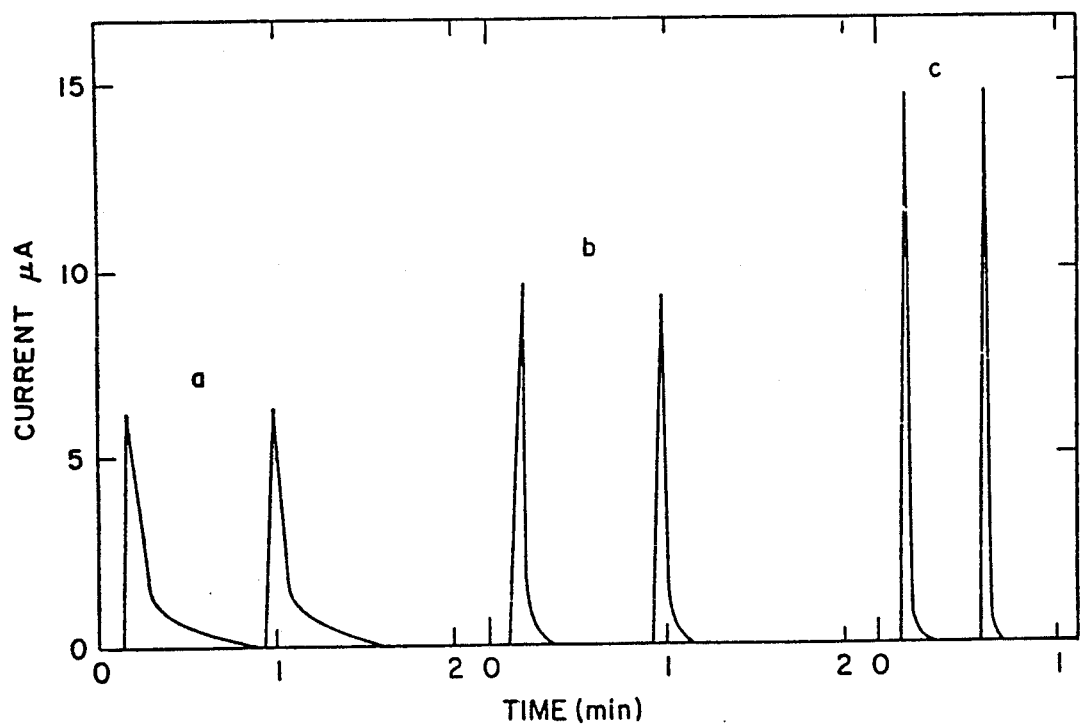
FIG — 3b
PRIOR ART

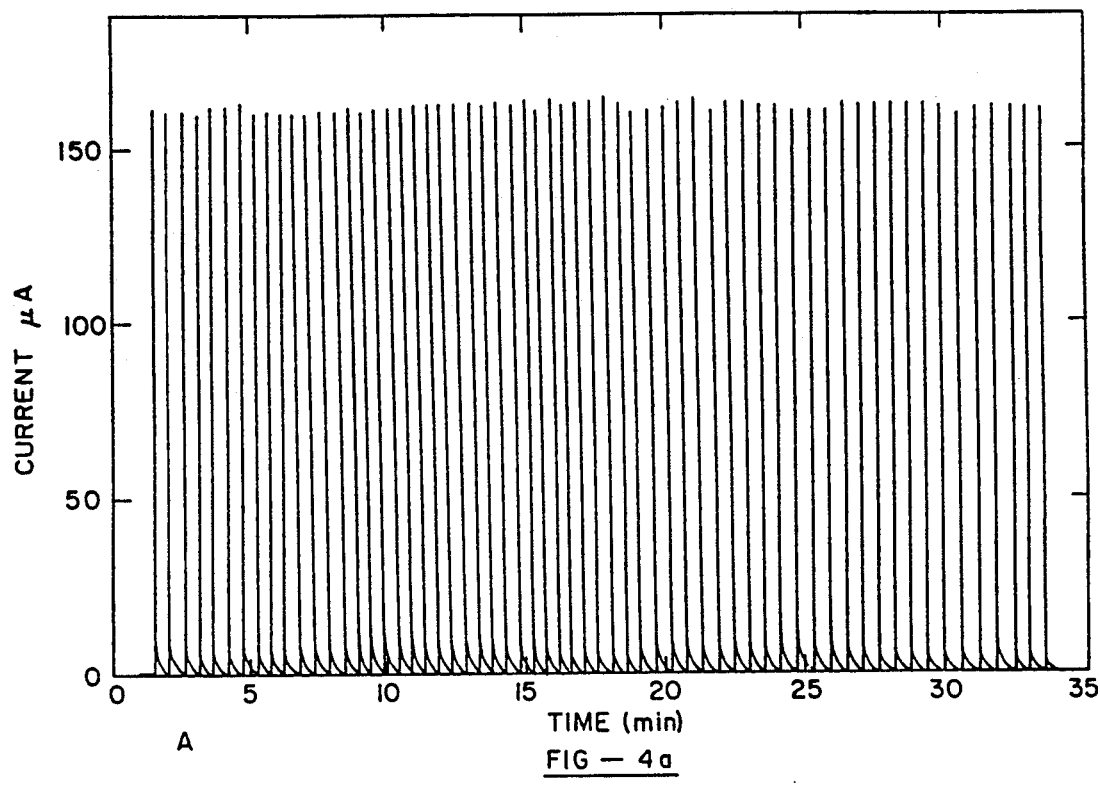
FIG — 4a
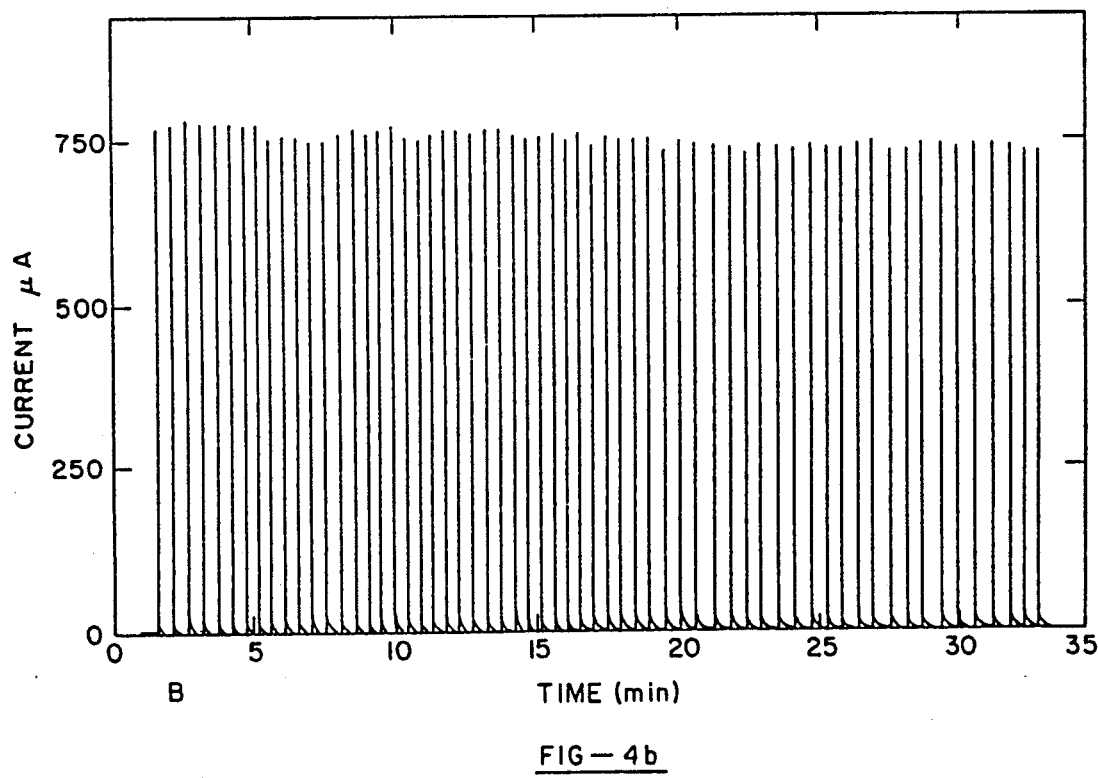
FIG — 4b

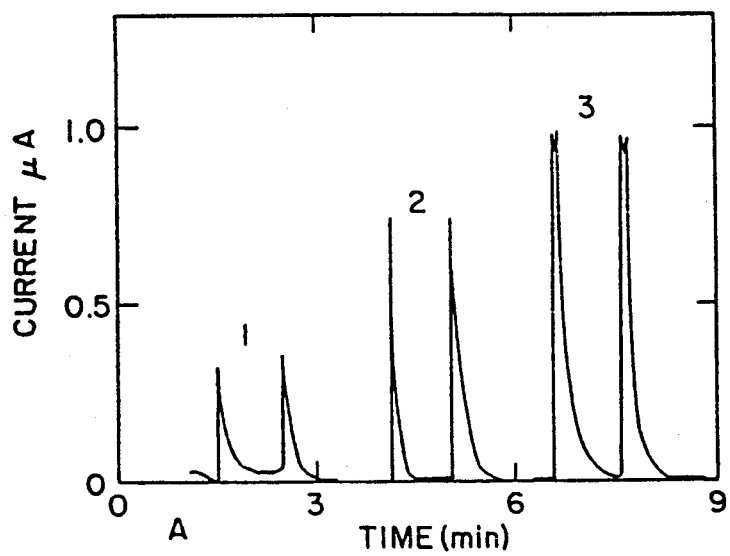
FIG—7a
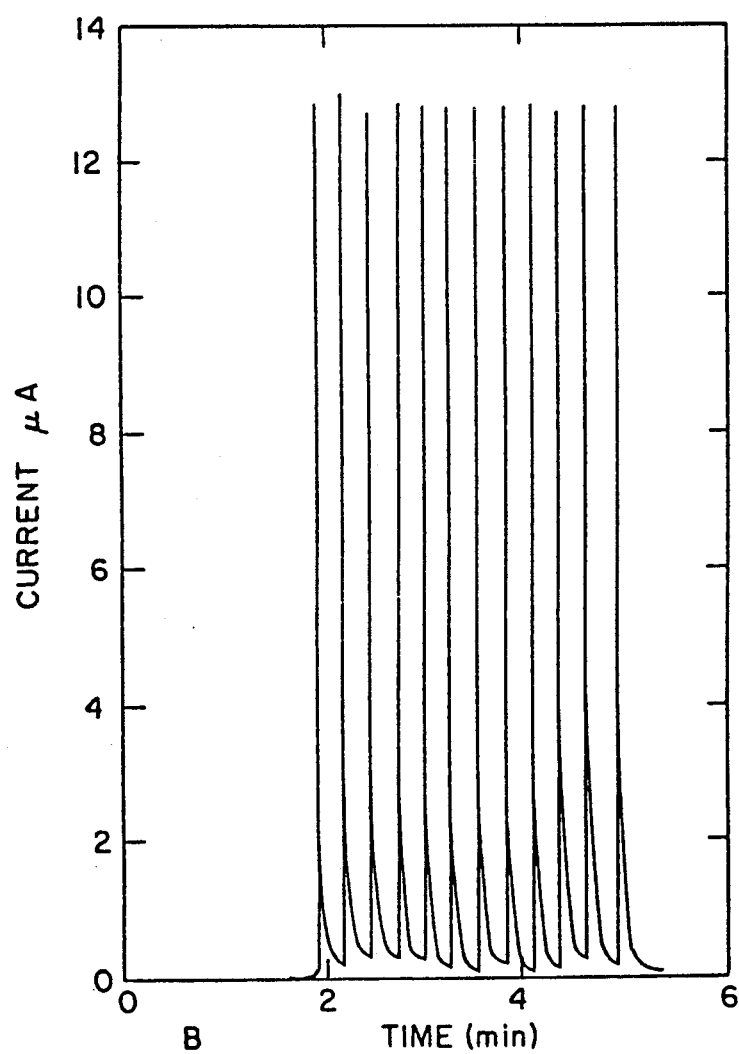
FIG—7b

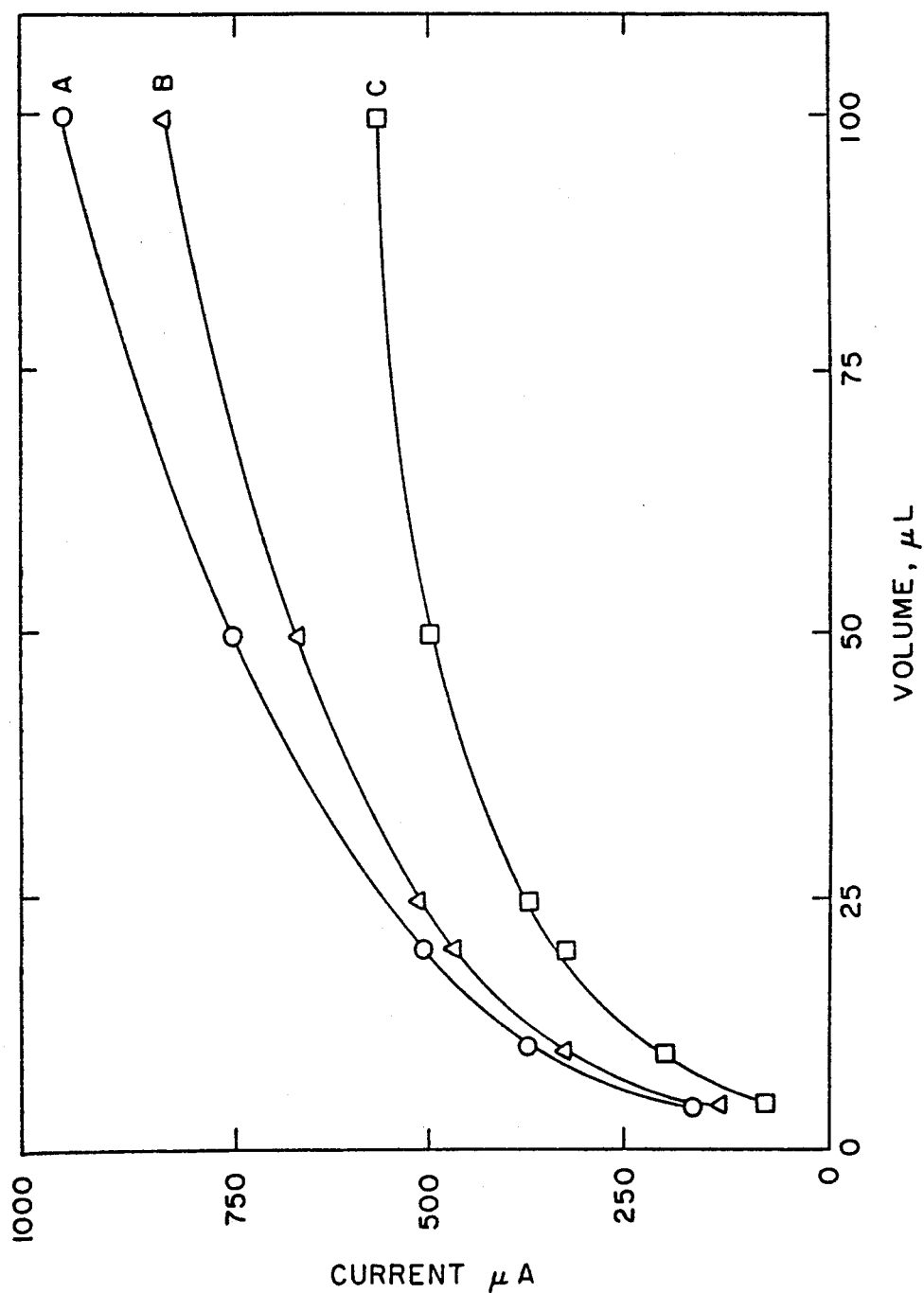

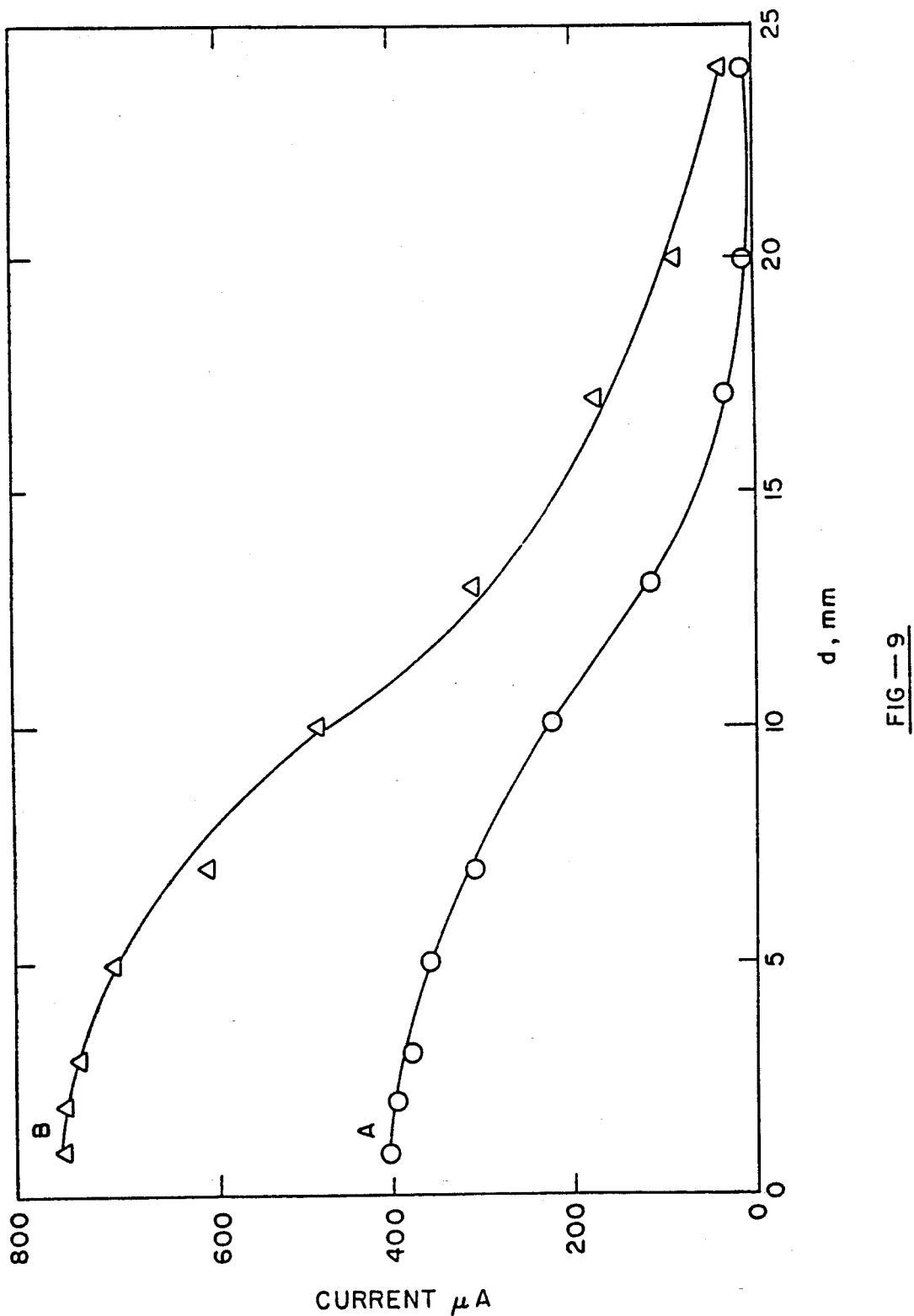
FIG—9

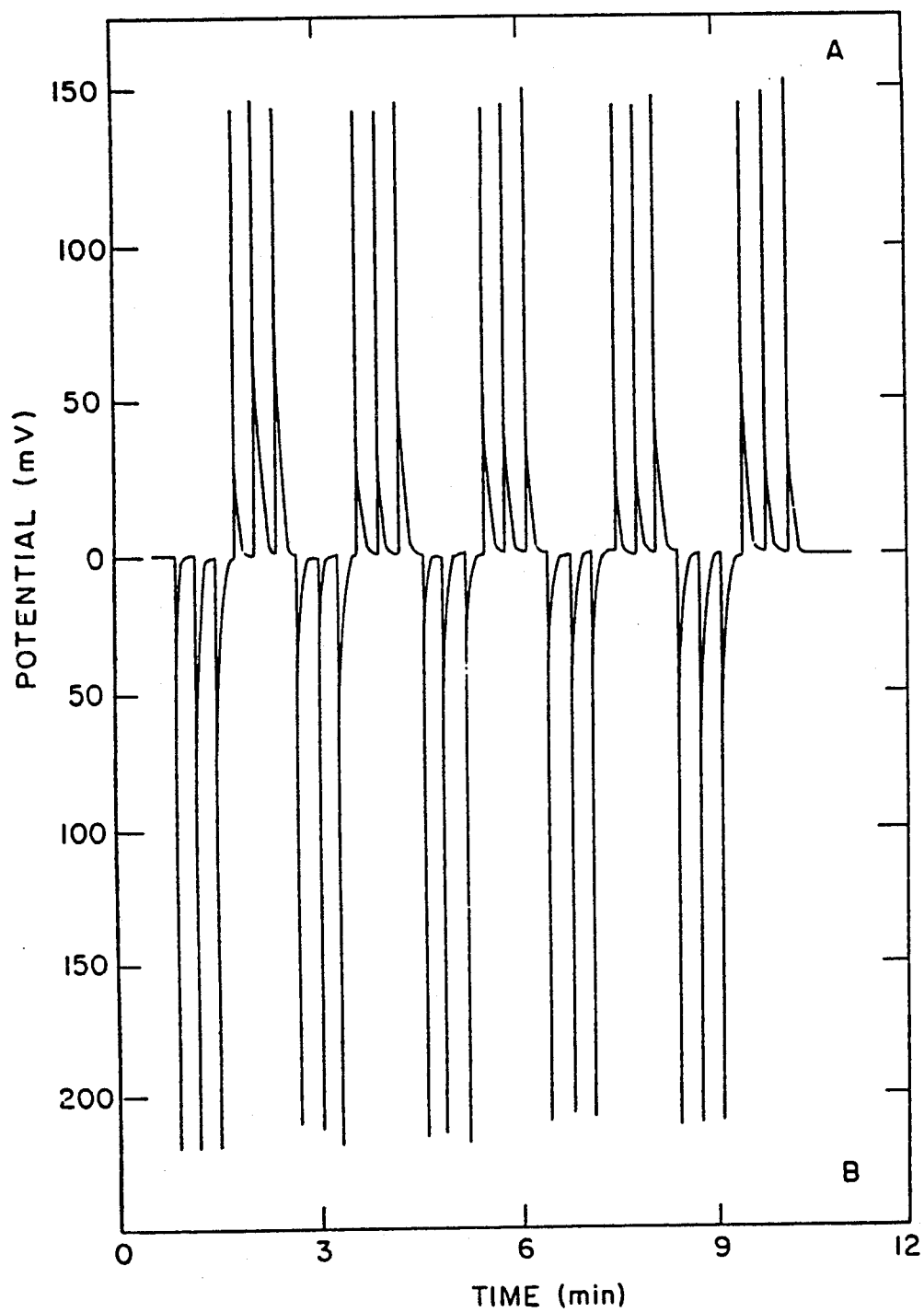
FIG—11

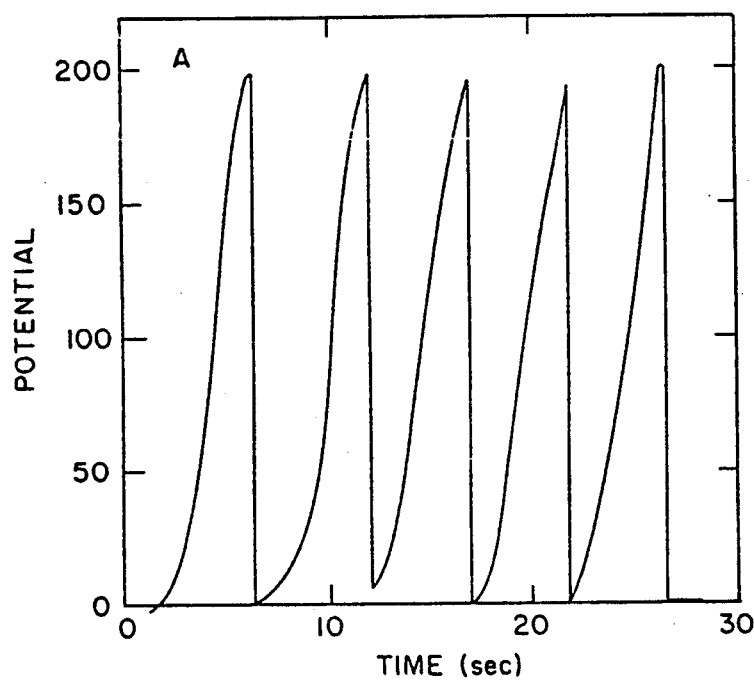
FIG—12a
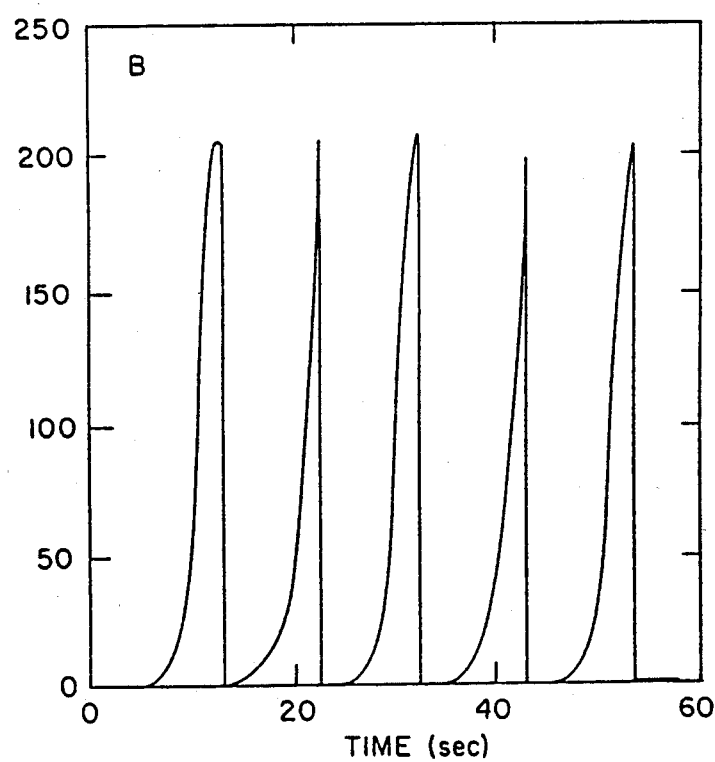
FIG—12b

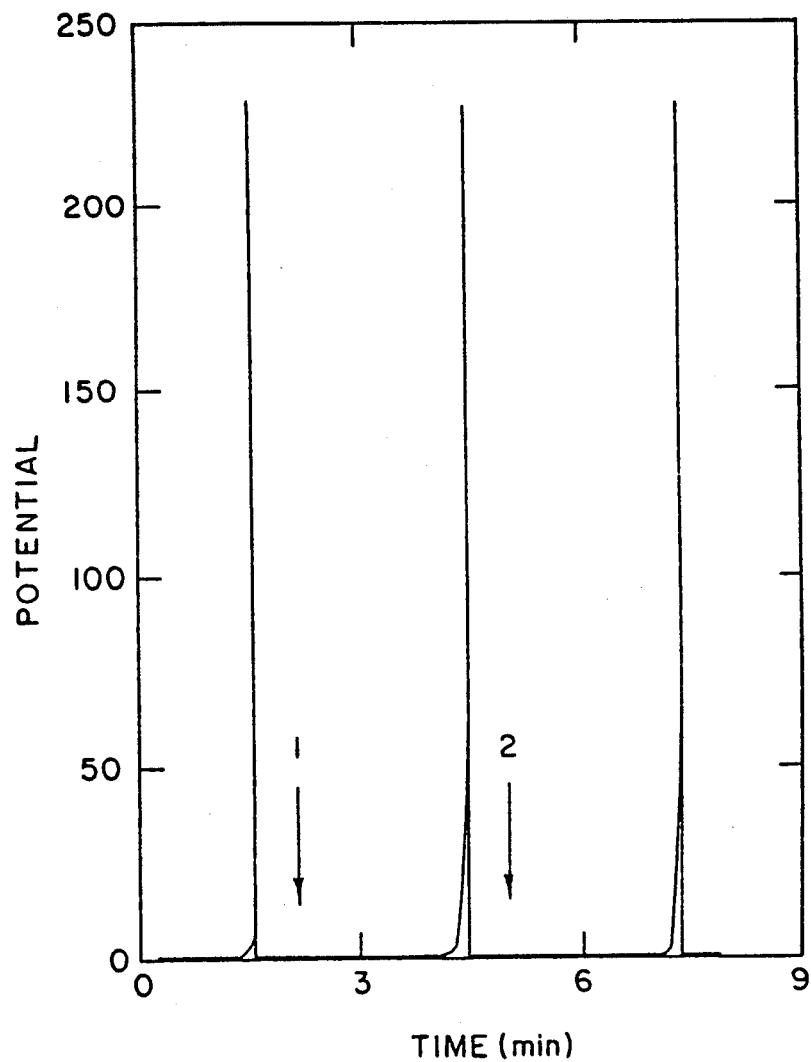
FIG — 14

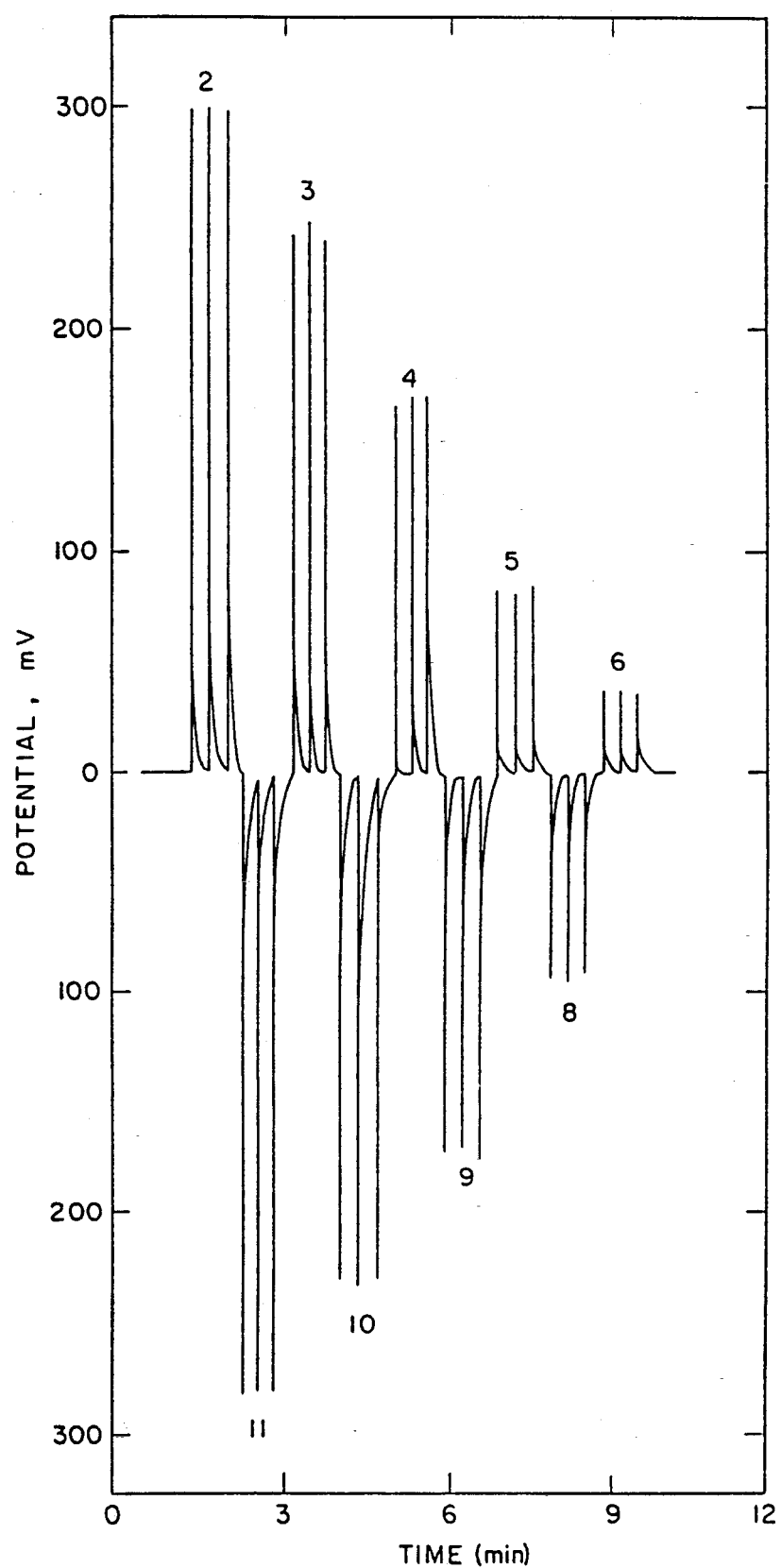
FIG—15

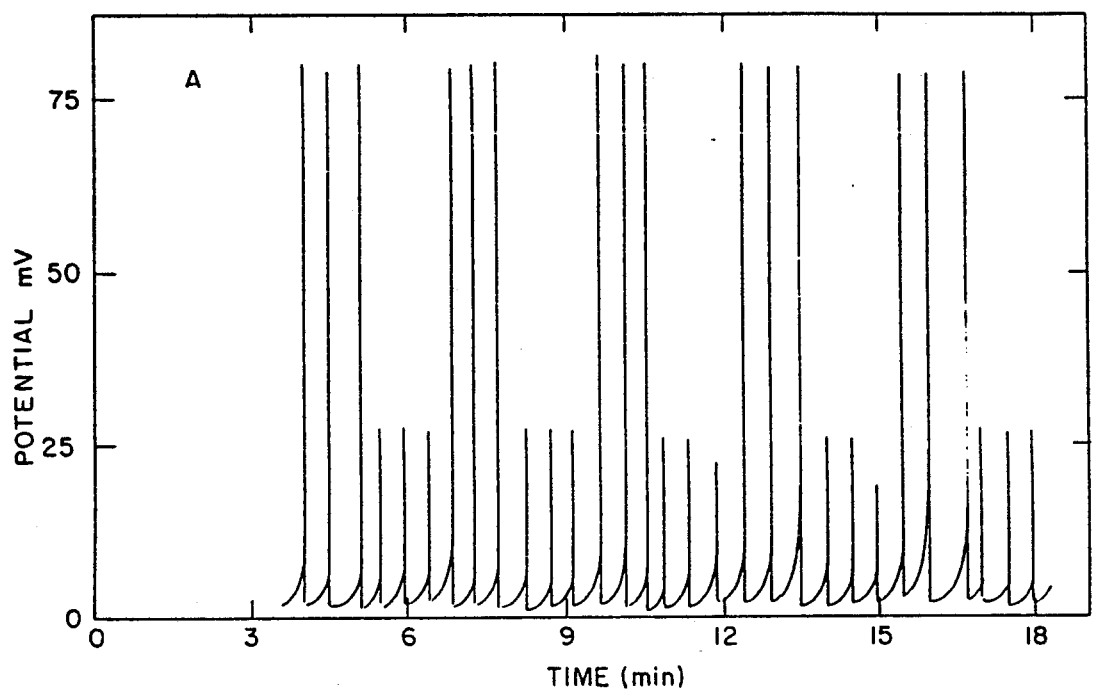
FIG—17a
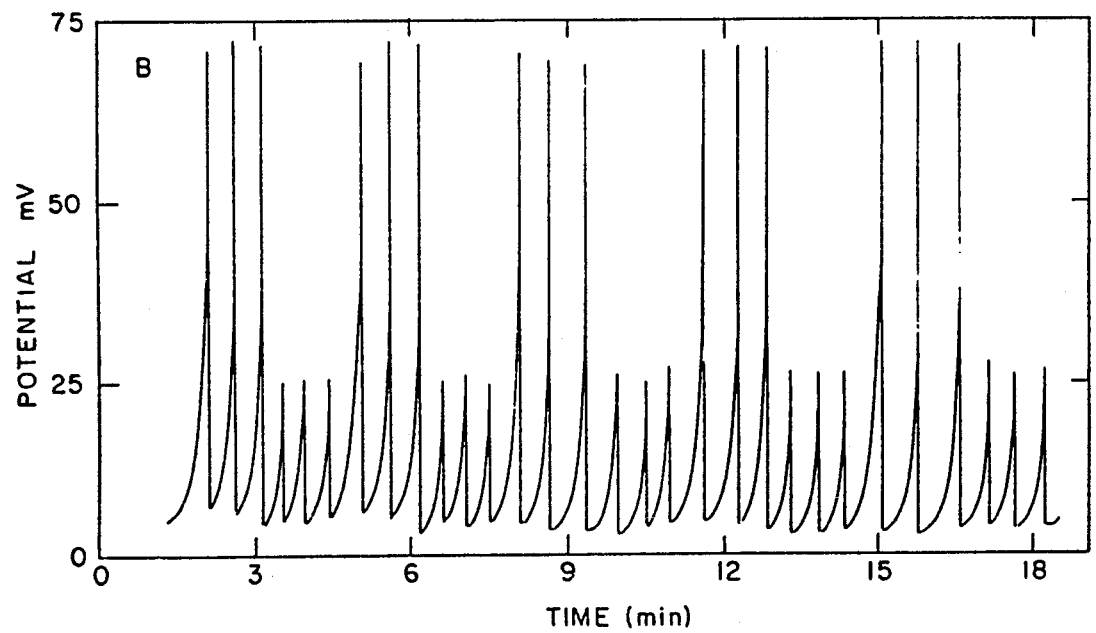
FIG—17b

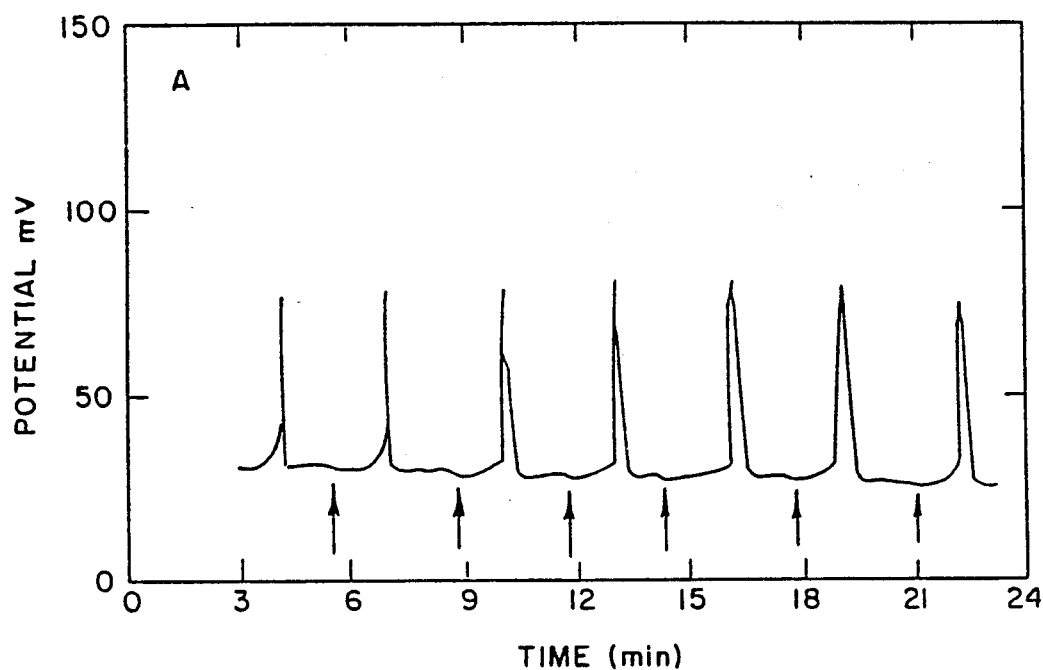
FIG — 18a
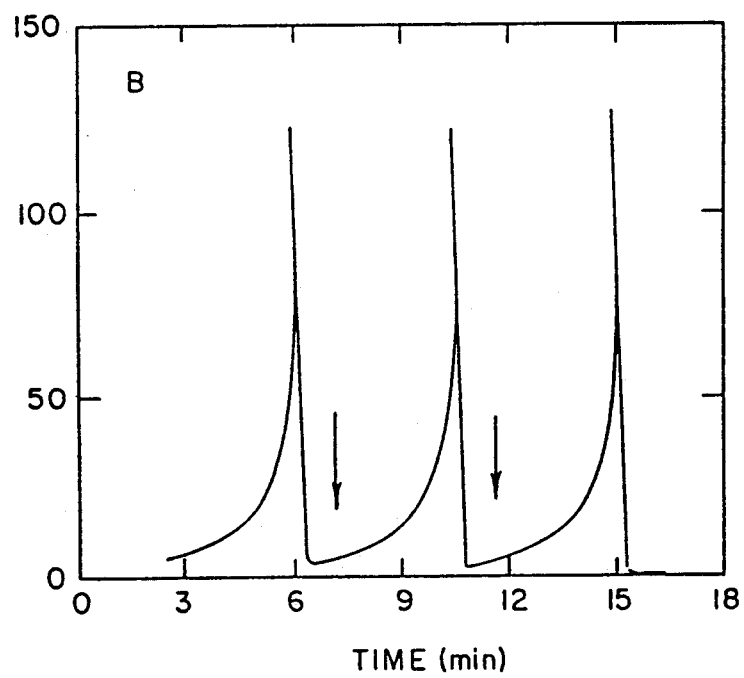
FIG — 18b

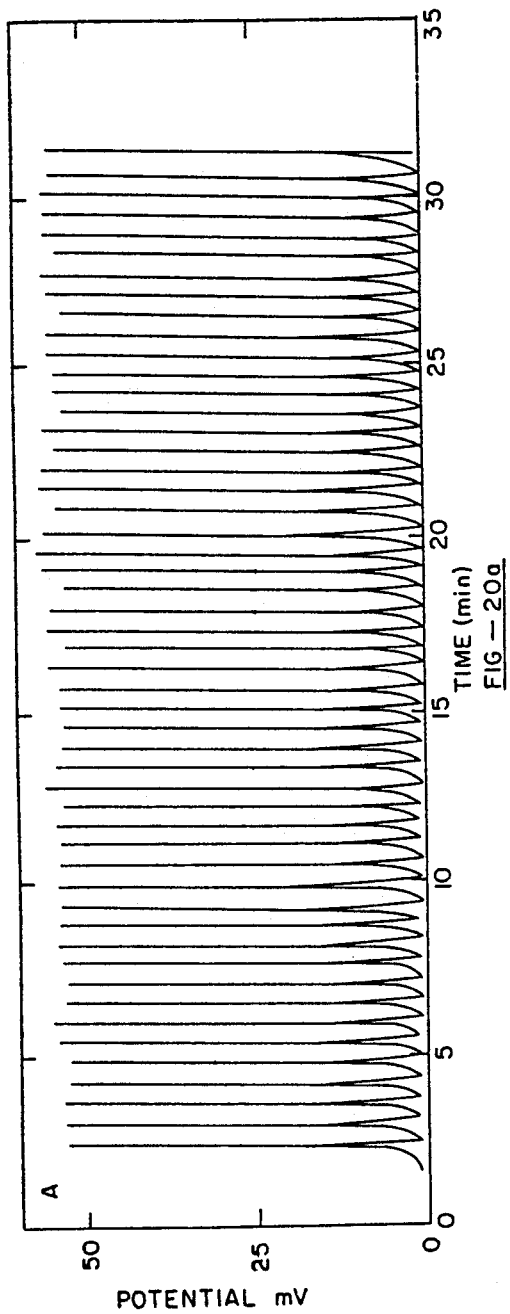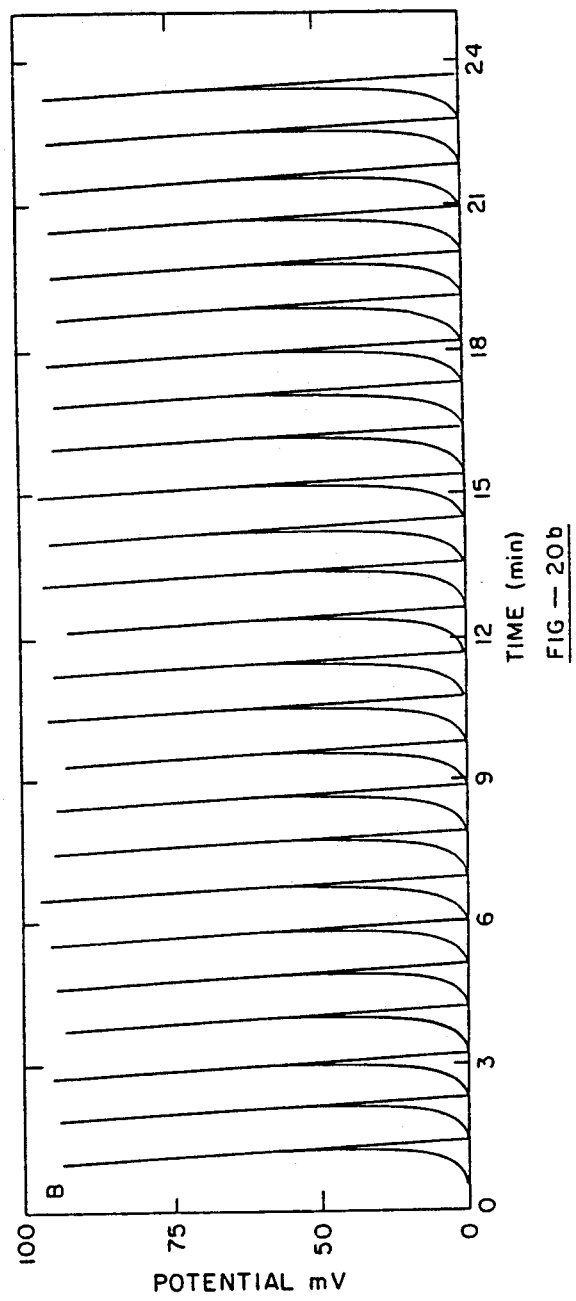

METHOD AND APPARATUS FOR BATCH INJECTION ANALYSIS

BACKGROUND OF THE INVENTION

1. Field of the Invention (Technical Field)

This invention relates to apparatuses for measurement of analytes injected into a static electrochemical cell and a method for its use.

2. Background Art

Several different techniques for measurement of analyte concentration have evolved in the prior art. Notable among these techniques is flow injection analysis (FIA). In this measurement process, a sample to be analyzed is injected into a laminarly flowing carrier stream of solvent and reagents. Reproducible sample volumes are injected, so the reaction need not proceed to the steady state. The reaction is developed only to the point which permits recordation as the sample passes an appropriate detector. The output transient signals thus produced reflect the concentration of the injected analyte. Flow injection analysis is described in articles entitled "Flow Injection Analysis: New Tool for Old Assays—New Approach to Analytical Measurements," by Kent K. Stewart (*Analytical Chemistry*, Vol. 55, No. 9, Aug. 1983) and "Flow Injection Analysis: From Test Tube to Integrated Microconduits," (*Analytical Chemistry*, Vol. 55, No. 11, Sep. 1983); and in the Lachat brochure entitled "The FIA Concept.," the Tecator brochure on the FIAstar Flow Injection Analysis Bibliography., and the Control Equipment Corporation brochures entitled "The Applications: What it Does."

Obvious disadvantages are present with flow injection analysis. Pumps, valves, and tubing are required. Further, chemical reaction is often required to convert the analyte to a detectable species.

Other quantitative analysis apparatuses are taught by the prior art. U.S. Pat. No. 4,865,992, entitled *System and Method for Quantitative Analysis of a Solution*, to Hach, et al., teaches such apparatus comprising continuous addition of reagent to a beaker containing a chemical species to be measured until an endpoint is reached. This procedure requires a chemical reaction, large samples, and involves a slow measurement of reaction product.

U.S. Pat. No. 4,695,555, entitled *Liquid Chromatographic Detector and Method*, to O'Keeffe, involves "spray electrification" wherein droplets of an analyte acquire electric charges dependent upon the concentration of solute carried by the droplet. Measurement of concentration of solute is enabled by measurement of the amount of deviation of the droplets from a neutral path. U.S. Pat. No. 4,003,705, entitled *Analysis Apparatus and Method of Measuring Rate of Change of Electrolyte pH*, to Buzza. et al., teaches specific measurements of $CO_2$ and chloride in blood, based on reaction with an electrolyte and subsequent pH measurement.

International Application No. PCT/DK89/00070. entitled *A Method of Effecting NIR-Analyses of Successive Material Samples, and a System for Carrying Out the Method*, to Johnsen, discloses a near-infrared reflection spectroscopy apparatus wherein the effect of remnant deposits is avoided by an advancing film between test chamber and optical unit.

Thus, it is seen that the prior art lacks a fast, repetitive, highly reproducible, versatile, and reliable analytical measurement system devoid of conduits, valves, and pumps.

SUMMARY OF THE INVENTION
(DISCLOSURE OF THE INVENTION)

The present invention comprises a method and apparatus for measuring analyte sample concentration. The apparatus of the invention comprises a vessel, electrolyte confined within the vessel, an entry for introducing analyte samples to be analyzed into the vessel, a detector in the vessel for sensing the analyte samples to be analyzed, and an analyzer for analyzing the analyte samples.

In the preferred embodiment of the invention, the vessel further comprises a stirrer, and preferably a magnetic stirrer. The electrolyte is preferably inert relative to the analyte sample, and preferably comprises a solution such as potassium chloride, a phosphate buffer and sodium hydroxide, potassium dihydrogen phosphate and sodium nitrate, and $CH_3COONa$, $CH_3COOH$, $NaCl$, and 1,2 diaminocyclohexane-N,N,N',N', tetraacetic acid, such as a solution comprising $CH_3COONa$, $CH_3COOH$, $NaCl$; 1,2 diaminocyclohexane-N,N,N',N', tetraacetic acid; and aluminum sulfate. Preferably analyte samples are introduced into the vessel by injection, such as using a pipette. The detector preferably comprises an electrode. The electrode may be spherical or planar, may comprise carbon paste (which may further comprise glucose oxidase and/or ruthenium dioxide), may be a pH electrode, or an ion-selective electrode (such as a chloride or fluoride electrode). The analyzer for analyzing the analyte samples preferably comprises amperometric or potentiometric measuring devices. In most applications, the samples to be analyzed are introduced and sensed within 2 to 10 mm from each other. However, for other applications the distance is preferably less than 2 mm or greater than 10 mm.

The method of the invention comprises the steps of:
a) providing a vessel;
b) confining an electrolyte within the vessel;
c) introducing samples to be analyzed into the vessel;
d) sensing the samples to be analyzed; and
e) analyzing the samples.

A primary object of the invention is the provision of a highly reproducible and repetitive analyte measurement apparatus and method using a confined, inert, large volume electrolyte.

Yet another object of the invention is the provision of an analyte measurement apparatus and method which relies on specific sensing surfaces.

Still another object of the invention is to provide a batch injection analysis apparatus and method with performance equivalent to flow injecting analysis.

An advantage of the invention is the provision of a reliable analyte concentration apparatus totally devoid of pumps, conduits, and valves.

Another advantage of the invention is the provision of rapid "wash out" and dispersal of samples.

Still another advantage of the invention is the provision of analyte sample apparatus and method amenable to amperometric or potentiometric measurements.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention.

FIG. 1 is a schematic diagram of a batch injection analysis (BIA) vessel with amperometric detection;

FIGS. 2(a)-2(c) depict sample injection in BIA;

FIGS. 3(a) and 3(b) illustrate a comparison between BIA and FIA;

FIGS. 4(a) and 4(b) depict repetitive injections of hydroquinone and ferrocyanide in solutions;

FIGS. 7(a) and 7(b) depict responses for glucose using biologically and chemically modified electrodes;

FIG. 8 depicts effects of sample volumes upon different electrode distances;

FIG. 9 also depicts effects of sample volumes upon different electrode distances;

FIG. 11 is a comparison of responses obtained with high and low pH injections;

FIGS. 12(a) and 12(b) are comparisons of the response for different injection rates;

FIG. 14 depicts responses for sample injections followed by massive addition of sample solutions;

FIG. 15 shows responses for sample injections of varying pH;

FIGS. 17(a) and 17(b) depict comparison responses for low and high concentration of chloride and fluoride injections;

FIGS. 18(a) and 18(b) depict comparison results for chloride and fluoride solutions with massive additions of such chloride and fluoride solutions;

FIGS. 20(a) and 20(b) depict responses for repetitive injections of fluoride and chloride solutions.

Figure 5:
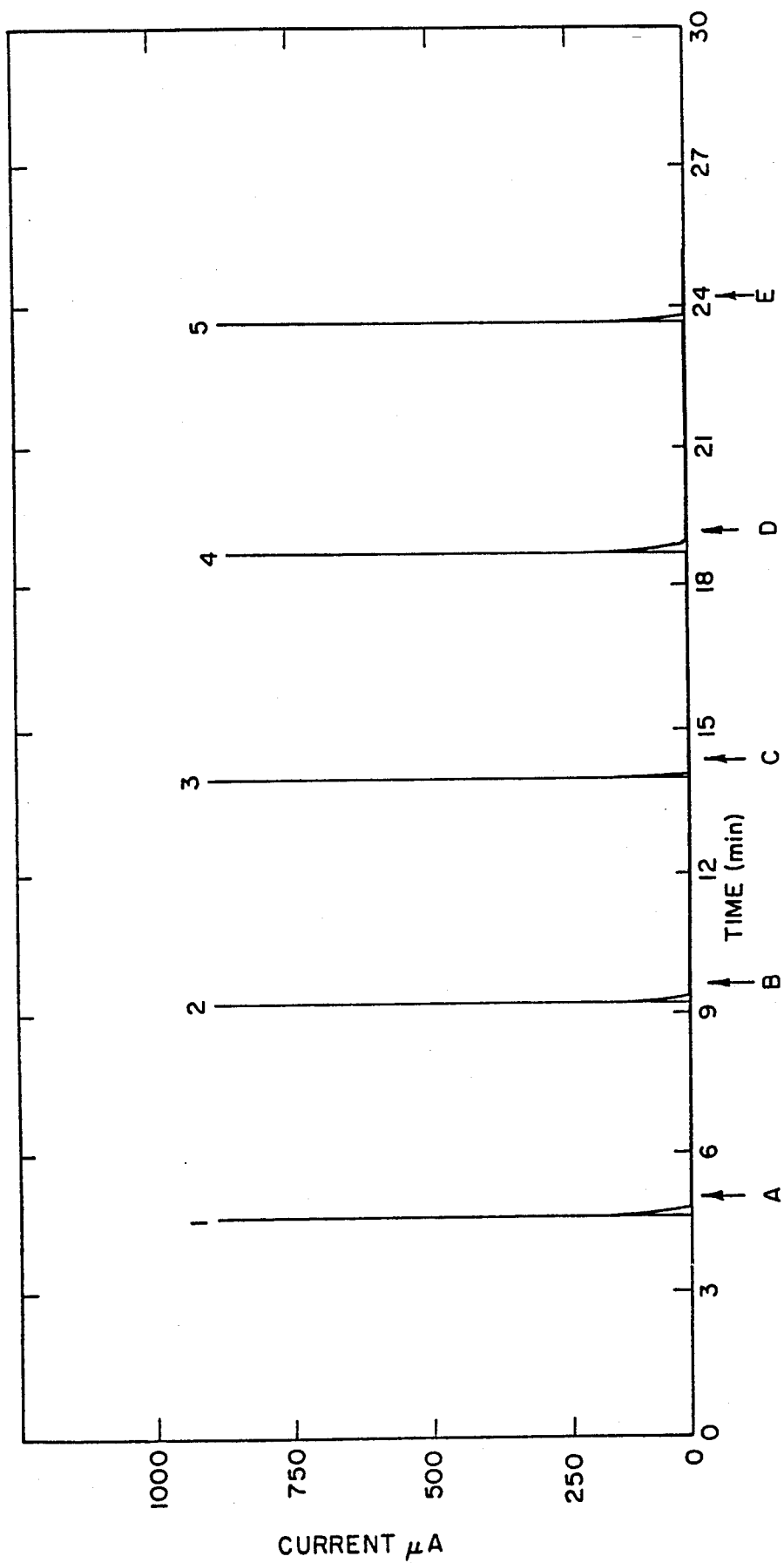
FIG. 5 depicts five injections of ferrocyanide, each injection followed by massive additions of ferrocyanide.

DESCRIPTION OF THE PREFERRED EMBODIMENTS (BEST MODES FOR CARRYING OUT THE INVENTION)

Reference is now made to FIG. 1 which depicts the apparatus of the preferred embodiment of the invention. The apparatus comprises a cell 10 preferably made of a non-reactive material, such as PLEXIGLAS®, LEXAN®, LUCITE®, or the like. Working electrode 11 is inserted from the bottom of cell 10 and retained in position by a glass seal, for example, a Wilson glass seal, or the like. Pipette or micropipette 12, such as an Eppendorf standard pipette, or the like, is likewise retained in position on cell cover 13 by an indexed clamp (not shown) so as to assure a reproducible position, or more importantly, to assure a reproducible working electrode 11-pipette 12 tip separation distance 14. Counter electrode 15, usually platinum or other conductive noble metal, and reference electrode 16 are also mounted on cell cover 13 and complete the measuring circuit.

Working electrode 11 and electrode tip 11' preferably comprise carbon paste (55% graphite powder, 45% mineral oil) or platinum disks. Other electrodes, including ion-selective electrodes, biological and chemical modified electrodes, as well as optical (fiber-optic) or thermal sensors, can be used.

Aperture 17, closed by stopper 18, in cover 13 provides access for introducing and replenishing the cell solution, a relatively "inert" electrolyte. ("Inert," as defined herein with respect to the electrolyte, means that although the electrolyte is ionically dissociative, the electrolyte is for all practical purposes chemically unreactive with the analyte or sample.) The cell is drained through drain 20. Magnetic bar 19 provides agitation when cell 10 is placed upon an energized magnetic stirrer (not shown). Alternatively, an internal stirrer or agitator could be provided.

Electrodes 11, 15, and 16 are connected in circuit to a voltammeter, for example, an EG&G PAR model 364A, or the like. The output of the voltammeter is displayed upon a strip-chart recorder, for example, a HOUSTON OMNISCRIBE, or the like (not shown).

In operation, batch injection analysis (BIA) resembles flow injection analysis (FIA) in that an injected sample is transported in reproducibly consistent fashion toward a detector. In batch injection analysis, this is accomplished by placing the injector outlet (the tip of pipette 12) in close proximity to the sensor or detector surface 11'. The sample thereby literally floods the detector surface.

In addition to reproducible and consistent transport over the detector surface, batch injection analysis requires effective "wash-out" characteristics. This is accomplished in the preferred embodiment of the invention by the use of a large-volume stirred cell solution. Thus, small samples (20-50 μL) are rapidly dispersed and greatly diluted (20,000-50,000 fold) over the entire cell volume, permitting a great number of repetitive tests with no "build-up" of analyte.

In the preferred embodiment of the invention, injection action of the sample through the pipette 12 provides convective transport toward the detector surface 11'. Accordingly, batch injection analysis resembles a stopped-flow operation with samples flowing toward the detector surface 11', but no flow of the cell solution or electrolyte occurs.

FIGS. 2(a), 2(b), and 2(c) illustrate in an enlarged view, in succession, injection and transport of a sample from the tip of pipette 12 toward the surface 11' of detector electrode 11, and subsequent dispersion of the sample. Flat-surface electrodes, especially those of planar-disk configuration, appear quite effective in radial spread assuring activity only at the surface of the electrodes, even at relatively large pipette tip-electrode separations, as well as effective washout.

EXAMPLES (INDUSTRIAL APPLICABILITY)

The invention is further illustrated by the following non-limiting examples using a cell approximately 10×10 cm square with a height of approximately 8 cm, with a cell capacity of approximately 700 mL.

EXAMPLE 1

FIGS. 3(a) and 3(b) depict a current vs. time comparison of batch injection analysis (BIA) and flow injection analysis (FIA), respectively. The analyte comprised 20 μL samples of $1 \times 10^{-4}$ M ferrocyanide. Different stirring rates for BIA were used: a) 0 rpm; b) 250 rpm; and c) 500 rpm. The flow rates for FIA were: a) 0.2 mL/min.; b) 0.5 mL/min.; and c) 1 mL/min. In both instances, the cell electrolyte was 0.1 M KCl; the electrode-tip distance (in BIA) was 2 mm. Both BIA and FIA resulted in sharp peak readouts with good resolution. A notable distinction, however, is evident in the peak broadening which occurred with FIA due to dispersion in the flow channel. In contradistinction thereto, the peak sharpness of BIA resulted from rapid "wash-out" due to stirring. The peak widths (after dispersion) are 1.4, 1.2, and 1.0 seconds for 0, 250, and 500 stirring rpm, respectively. The latter stirring speed corresponds to a sample injection rate of 720 samples per hour. Further, the data of the example indicated that batch injection analysis compared favorably with flow injection analysis in terms of sensitivity and detection limits.

EXAMPLE 2

FIGS. 4(a) and 4(b) illustrate repetitive sample testing using ferrocyanide (FIG. 4(a)) and hydroquinone (FIG. 4(b)) solutions. Sixty repetitive samples of $5 \times 10^{-4}$ M ferrocyanide and hydroquinone were injected into a cell containing 0.1 M KCl as electrolyte for the ferrocyanide and 0.1 M phosphate buffer for hydroquinone. The graphs indicated no apparent change in peak currents, response times, or baseline. The standard deviations, 1.6% for ferrocyanide and 1.1% for hydroquinone, compared favorably with the flow injection analysis technique. It is believed this consistency is largely attributable to micropipette-based injections, albeit manual. Consistency may be improved using robotic injection.

Further, this example demonstrated that the "build-up" of sample solutions does not affect batch injection analysis. This fact is attributed to the great dilution factor as well as the fact that the cell solution or electrolyte is inert relative to the electrode.

EXAMPLE 3

FIG. 5 further illustrates the fact that sample build-up does not affect batch injection analysis performance. In this example, 20 μL of 50 mM ferrocyanide solution samples were injected over a 20 minute period (peaks 1-5 represent such injections) The electrolyte again was 0.1 M KCl and stirring rate was 250 rpm. Additionally, after each injection, a 2 mL volume of the same solution was added (A-E) from hole 17 in cover 13 (FIG. 1). Although each such addition was equivalent to 100 injections, the batch injection analysis peak currents remained essentially the same, and no baseline drift was observed. Deterioration of the baseline was observed only after 400-500 equivalent injections (near point E). Since 500 repetitive injections are normally standard under flow injection analysis, this represents a highly consistent and satisfactory performance. Drainage and replacement of electrolyte is thus indicated after approximately 500 repetitive injections, or by baseline deterioration.

EXAMPLE 4

Figure 6:
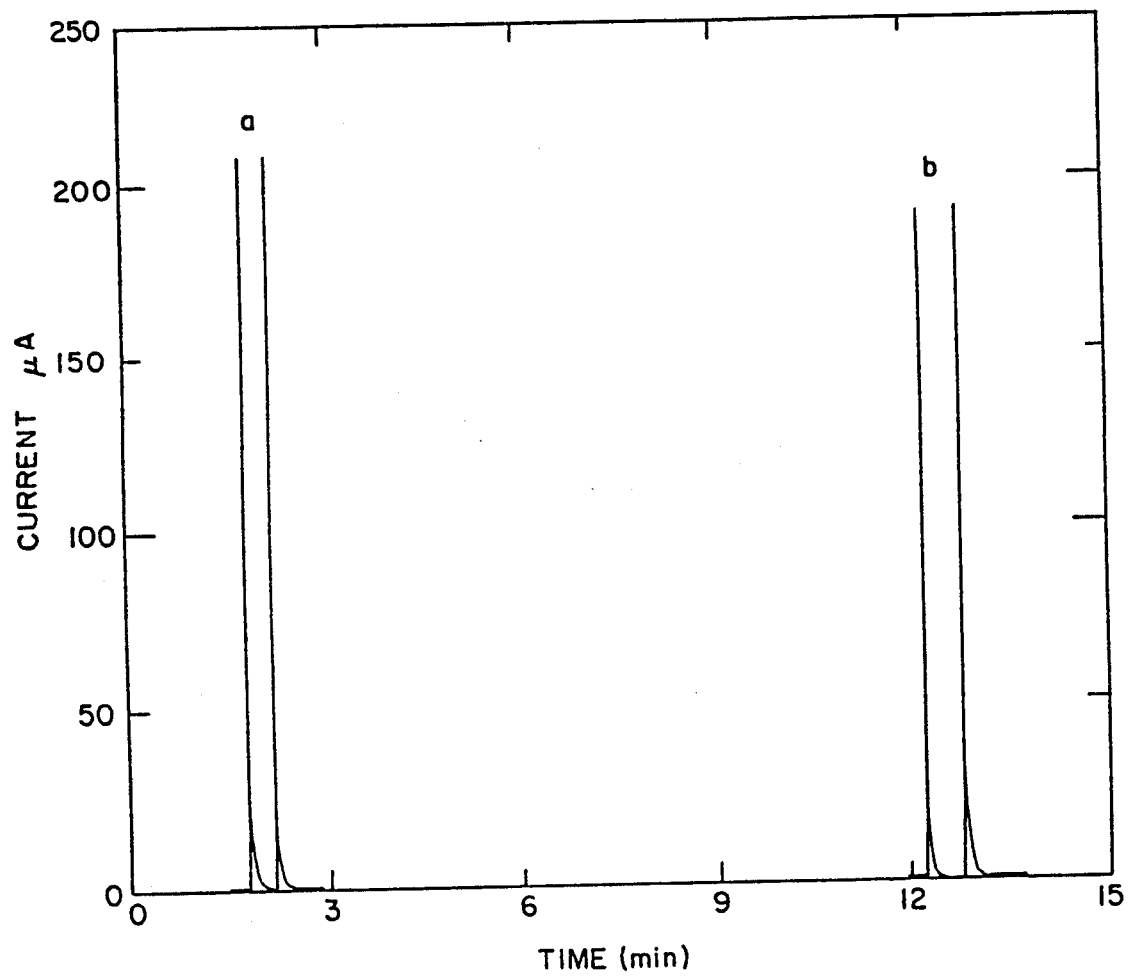
FIG. 6 depicts the relative inertness of the electrolyte in BIA.

FIG. 6 depicts a comparison of two injected samples of $2.5 \times 10^{-4}$ M acetaminophen, one sample (a) containing 0.01 M KCl electrolyte, the other not. The cell solution was 0.01 M KCl and stirring rate was 250 rpm. As clearly indicated, a well defined and sensitive response was observed for sample (b). This example indicated great potential exists for assays of resistive or nonaqueous samples.

Batch injection analysis relies upon highly specific sensors or reactive sensor surfaces. With reactive sensor surfaces, reaction occurs at or in close proximity to the sensing surface. The analyte is thereby converted to a detectable species.

EXAMPLE 5

FIGS. 7(a) and 7(b) illustrate the use of an enzymatic electrode (FIG. 7(a)) comprising glucose oxidase (10%). and a non-enzymatic inorganic electrode (FIG. 7(b) comprising 20% ruthenium dioxide. Glucose concentrations in FIG. 7(a) represent three 50 μL injections ((1), (2), (3)) of 0.5 mM, 1.0 mM, and 1.5 mM, respectively. The electrolyte was 0.1 M phosphate buffer and 1 M NaOH. FIG 7(b) demonstrates that inorganic electrodes are also effective with carbohydrates. Obviously, other chemical and biological modifications of electrodes are possible. Other schemes include providing electrodes with selective coatings or membrane coverings, as well as optical or thermal devices, which may allow dilution, filtration, dialysis, and the like, on the detector surface.

EXAMPLE 6

FIG. 8 demonstrates variations of peak sensed current vs. injected volume, as well as current variation dependence upon electrode-pipette tip distance. The analyte was $5 \times 10^{-4}$ M hydroquinone: curve A corresponds to an electrode-tip distance of 2 mm; curve B corresponds to an electrode-tip distance of 5 mm; while curve C depicted results with a 10 mm tip-electrode separation. The electrolyte was 0.1 M phosphate buffer (pH 7.4). Currents increased rapidly to a volume of approximately 50 μL, then flattened somewhat. The data gave slopes of 0.4 on a log-log scale.

FIG. 9 corroborates this data. Curve A, representing a 10 μL sample of $5 \times 10^{-4}$ M hydroquinone, and curve B representing a 50 μL sample of $5 \times 10^{-4}$ M hydroquinone, both indicated decreasing responses with increased electrode-tip distances. Similarly, responses for 0.5 mM ferrocyanide (not shown) increased linearly with increasing radius (1-3 mm) of the electrode surface; again, the electrolyte was 0.1 M phosphate buffer.

Other factors affecting batch injection analysis response have been tested. Ten successive injections of 50 μL acetaminophen, hydroquinone, and ascorbic acid in increasing concentration (from 25 to 250 μM) were administered using a phosphate buffer electrolyte. In all cases, batch injection analysis response increased linearly with increasing concentration.

Amperometric peaks for injections of 20 μL solutions of $2.5 \times 10^{-6}$ M ascorbic acid and hydroquinone were used to estimate the detection limits, with an applied potential of +0.9 V. Signal-to-noise ratios of 50 and 30 were obtained at this trace level. Extrapolating to a signal-to noise ratio of 3, these data correspond to detection limits of $5 \times 10^{-8}$ M hydroquinone and $0.3 \times 10^{-8}$ M ascorbic acid: these are lower values than those obtained with analogous flow injection analysis measurements.

While amperometric measurements have generally been shown as providing excellent responses, other detection schemes are available. Potentiometric measurements using ion-selective electrodes, optical, or thermal sensors are particularly appealing. Such electrodes require little or no sample pretreatment. The high specificity of ion-selective electrodes renders such electrodes very attractive for batch injection analysis, where the lack of solution handling requires active or selective detectors.

Figure 10:
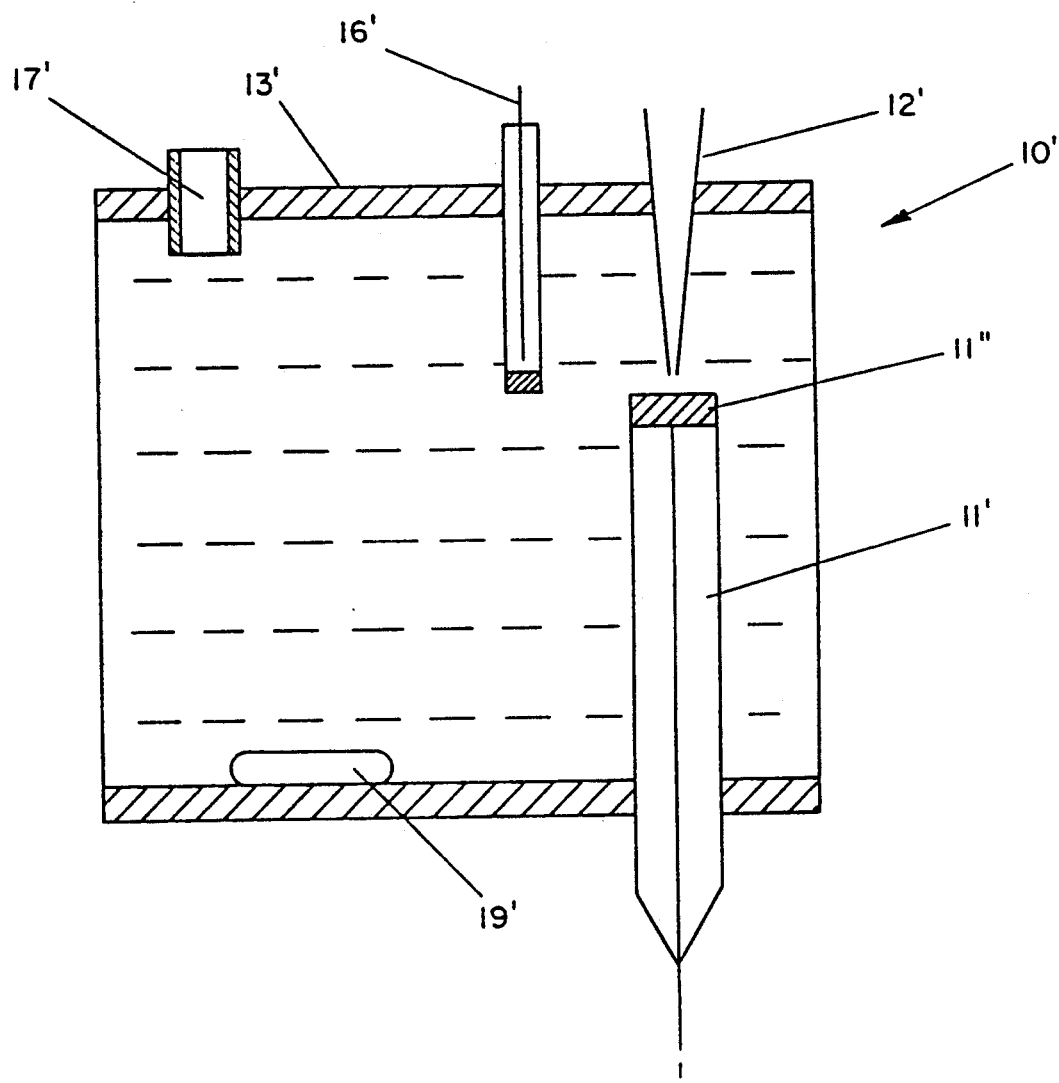
FIG. 10 is a schematic diagram of a BIA vessel used with potentiometric detection.

FIG. 10 depicts an electrochemical cell 10' suitable for potentiometric measurements. Ion-selective electrode 11' is inserted through the bottom of cell 10'. An aperture 17' in cover 13' was used for introducing, for example, a standard Eppendorf micropipette 12', the tip of which is positioned a known distance (usually 2 mm) from ion-selective electrode 11'. Reference electrode 16' (Ag/AgCl, for example, a model RE-1 from BAS, Inc.) is also mounted in cover 13'. Buffer solution and cell solution are added through aperture 17'. Magnetic stirring bar 19' is rotated by a magnetic stirrer (not shown) below cell 10'.

Potentiometric measurements were performed with an amplifier having a gain range of 2.5–1,000; the millivolt outputs were recorded in an OMNISCRIBE strip-chart recorder.

Both spherical (for example, a BECKMAN model 39831) and planar (for example, a MARKSON model 989B) electrodes were used for pH measurements. Fluoride and chloride electrodes (for example, ORION models 940900 and 941700, respectively) were used for fluoride and chloride concentrations, respectively.

All pH measurements were conducted with a cell solution of 0.1 M phosphate buffer containing 0.25 M potassium chloride (pH 7.00). Chloride measurements were performed in a 0.05 M $KH_2PO_4$ solution containing 0.25 M $NaNO_3$. The pH of such solutions was adjusted to 6 using NaOH. Fluoride experiments were performed in a solution containing 0.2 M sodium acetate, 0.17 M acetic acid, 0.35 M sodium chloride, and 1 gram/liter 1,2 diaminocyclohexane-N,N,N',N', tetraacetic acid (DCTA). Some fluoride measurements were performed in the presence of 0.5 mM aluminum sulfate. Juice samples (e.g., CAMPBELLS® Tomato Juice and SPICY HOT V8 ™ Juice) were filtered through a 0.45 μm filter before measurement. The coffee sample was prepared by dissolving 0.3g of MOUNTAIN BLEND ™ coffee in 25 mL of distilled water. Tap water was obtained from laboratory spigots.

EXAMPLE 7

FIG. 11 shows the responses obtained with sequential triple injections of 20 μL solution of pH 4 (A) and pH 10 (B) samples. Despite the great difference in hydrogen ion concentration, batch injection analysis shows no observable carryover. The sharp peaks and clear baseline indicate effective transport to and removal from the detector surface. Readout is within a few seconds following injection, indicating the possibility of high sampling rates. This is borne out by FIGS. 12(a) and 12(b), which indicate responses for pH 10 samples at a rate of 720 injections/hour (A) and 360 injections/hour, respectively.

EXAMPLE 8

Figure 13A:
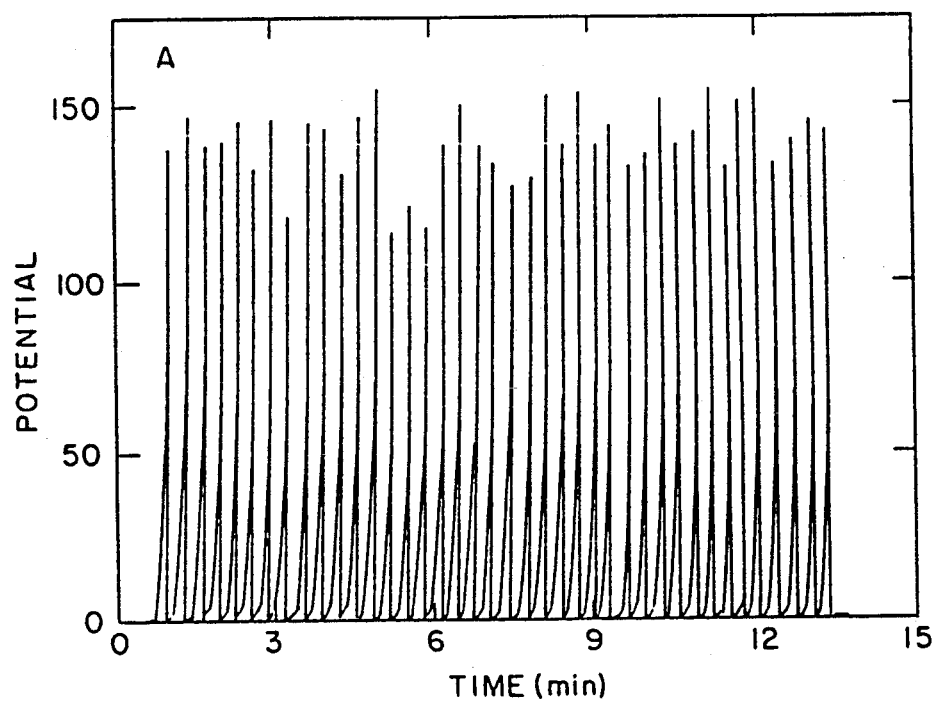
FIGS. 13(a) and 13(b) are comparisons of responses of spherical and planar electrodes.
Figure 13B:
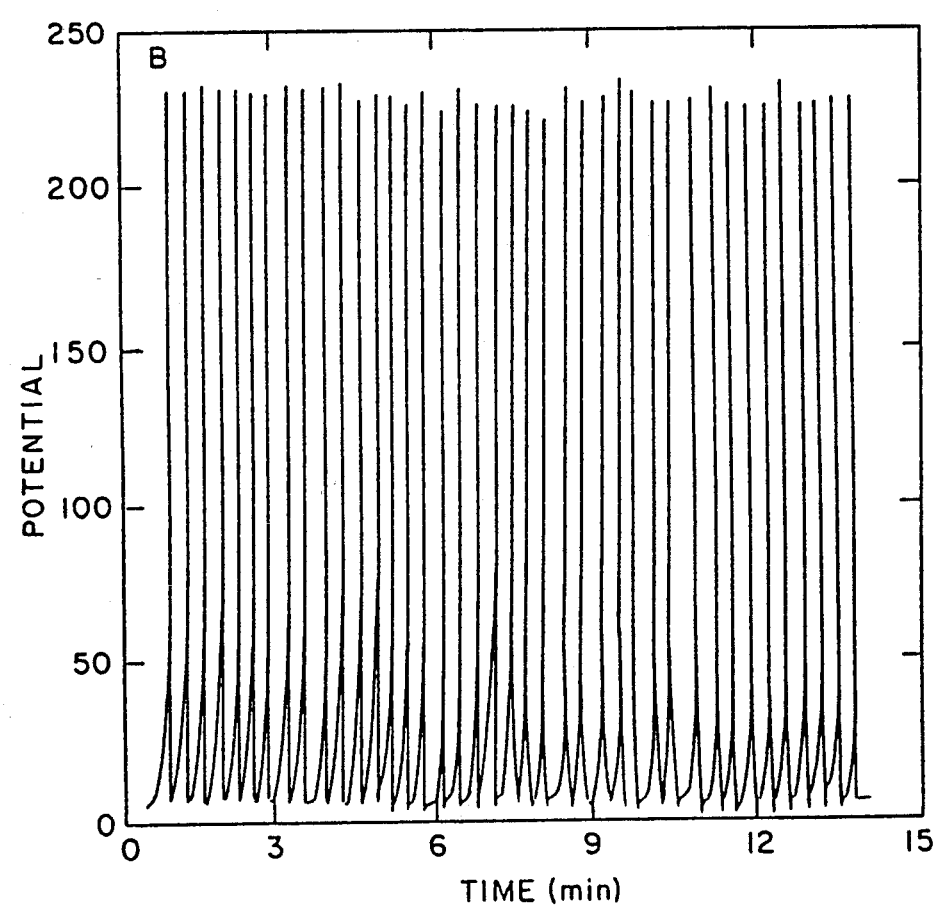

FIGS. 13(a) and 13(b) illustrate the criticality of flat ion-selective detection electrodes. Forty repetitive injections of 20 μL pH 10 solution using spherical (FIG. 13(a)) electrodes and flat (FIG. 13 (b)) electrodes gave the indicated responses. The flat electrodes yielded a relative standard deviation of 1.3%, while the spherical electrodes yielded a relative standard deviation of 6.8%. The superiority of flat electrodes insofar as reproducible response is thus demonstrated; it is believed that flat electrodes facilitate rapid "wash-out," or dispersion of sample. Again, automation of the injection process can further improve response.

EXAMPLE 9

FIG. 14 shows the results of three injections of 20 μL of pH 10 solution. At points (1) and (2), 6 mL of pH 2 solution was added through the port 17' in cover 13' (see FIG. 10). Despite the fact that each such addition was equivalent to 300 injections, peak potentials remained essentially the same and no baseline drift was observed. This lack of "memory" effect is believed due to the tremendous dilution capability of batch injection analysis.

EXAMPLE 10

FIG. 15 depicts the results of a series of different pH solutions injected in triplicate, alternating between high and low pH levels (pH 2–11). The batch injection analysis responses were quick and sharp The plot of peak potential vs. pH was linear (slope of 65 mV/pH, with a correlation coefficient of 0.998) not shown.

Figure 16:
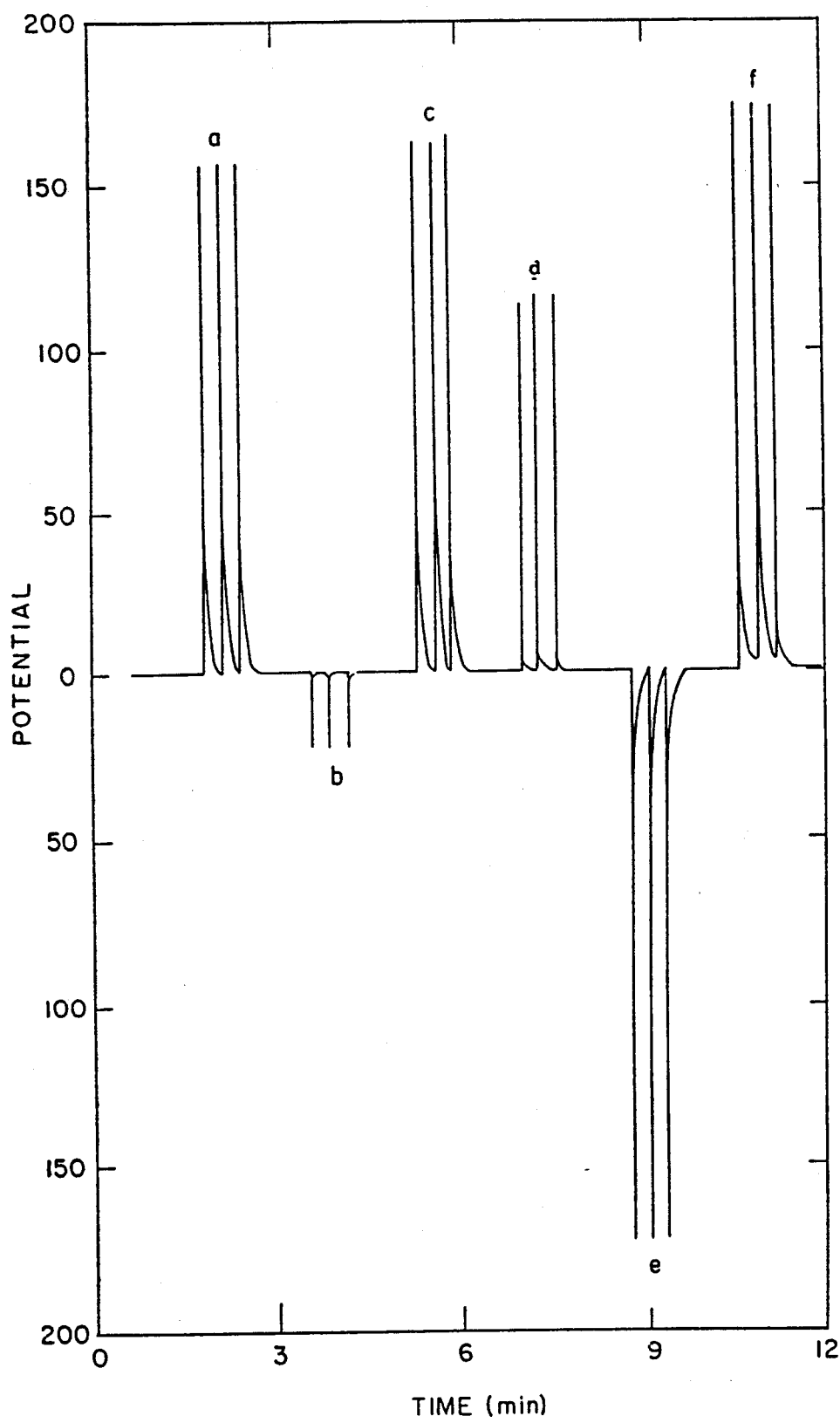
FIG. 16 shows responses for sample injections of common liquids of varying pH.

FIG. 16 depicts practical application of the above. CAMPBELLS® Tomato Juice (a), tap water (b), SPICY HOT V8 Juice (c), and coffee (d), gave the responses indicated against buffer standards of pH 10 (e) and pH 4 (f). Results were consistent with conventional pH measurement techniques.

EXAMPLE 11

FIGS. 17(a) and 17(b) depict "carryover" effects using chloride (FIG. 17(a)) and fluoride (FIG. 17(b)) ion-selective electrodes, respectively. Injection concentrations were in triplicate and alternatingly high (100 mM) and low (5 mM). The stirring rate for FIG. 17(a) was 0.300 rpm; for FIG. 17(b), 500 rpm. Sample volumes in all cases were 50 μL injected at a rate of 180/hour. The electrolyte solution for FIG. 17(a) was 0.05 M potassium dihydrogen phosphate ($KH_2PO_4$) and $NaNO_3$; the FIG. 17(b) cell solution was 0.2 M $CH_3COONa$; 0.17 M $CHC_3OOH$, 0.35 M NaCl, are 1 g/L DCTA (1,2 diaminocyclohexane-N,N,N',N', tetraacetic acid). The chloride electrode (FIG. 17(a)) gave faster responses, while the fluoride electrode (FIG. 17(b) was more sensitive. The rapid "wash-out" characteristics and fall off to the baseline are attributed to the planar electrode configuration coupled with the huge dilution factor. These data indicate that batch injection analysis can tolerate numerous injections with little or no memory effects.

This is further borne out by the data of FIGS. 18(a) and 18(b). Using the same cell solutions of FIG. 17, FIG. 18(a) depicts 100 mM chloride injections, while FIG. 18(b) shows the results of 0.5 mM fluoride injections. The arrows indicate massive additions of 2 mL of 100 mM chloride solution (FIG. 18.(a)), while in FIG. 18(b) the arrows indicate additions of 6 mL of 0.5 mM fluoride solution. Sample volumes in FIG. 18(a) were 50 μL; in FIG. 18(b), 20 μL. Additionally, the cell solution in FIG. 18(b) also contained 0.5 mM aluminum sulfate. Despite the "ramp" effect in FIG. 18(a), there was no effect upon the potential peaks. Similarly, in FIG. 18(b), the aluminum ion prevented a buildup of the fluoride ion concentration.

EXAMPLE 12

Figure 19:
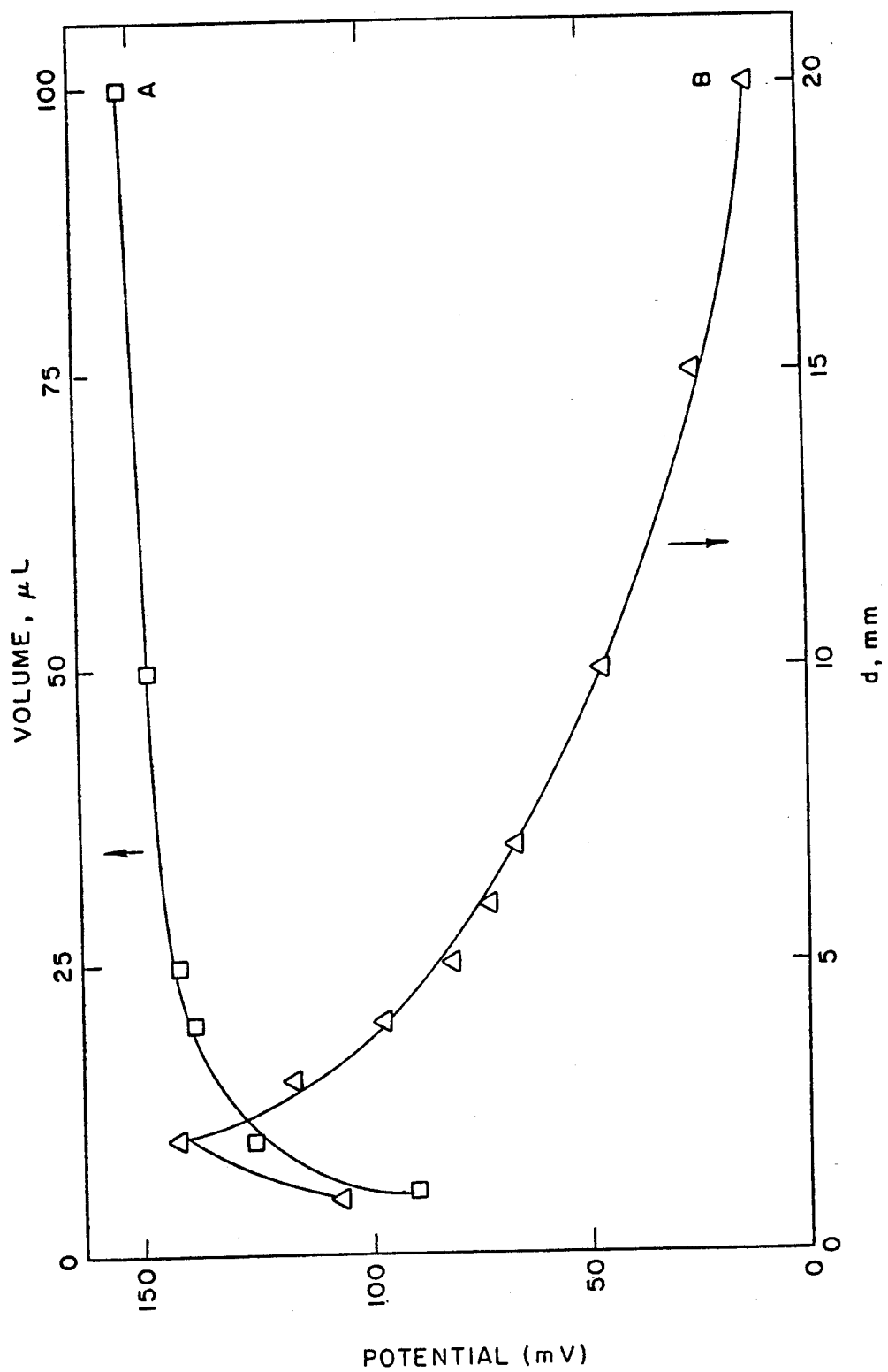
FIG. 19 shows effect of sample volume and tip-electrode distance upon response.

FIG. 19 depicts the effects of sample volume (A) and micropipette tip-electrode distance (B). On the response, similar had been obtained in voltammetric measurement. Peak potential response increased rapidly to 50 μL, then flattened. Response also increased sharply with tip-electrode distance (to 2 mm, after which response dropped rapidly) (FIG. 19(b)).

EXAMPLE 13

FIGS. 20(a) and 20(b) illustrate the high reproducibility of batch injection analysis using ion-selective electrodes. Two series of 50 and 20 repetitive injections of 25 mM chloride (FIG. 20(a)) and 1 mM fluoride (FIG. 20(b)), respectively, yielded responses with standard deviation of only 2.4% and 1.4%, respectively, even when injected at rates of 100 and 50 samples/hour, respectively. This again demonstrated that batch injection analysis can tolerate the presence of analyte in the cell even after numerous injections.

Although not illustrated, repetitive injections of 50 μL chloride and fluoride solution of concentrations of 0.5-10 mM and 10-5,000 μM ranges, respectively, were used to assess linearity and detection limits. Plots of peak potential vs. log-concentration were linear (slopes of 57.8 and 56.8 mV/decade, respectively). Detection limits of 0.1 mM (0.18 μg) chloride and 2 μM (2 ng) fluoride ions were estimated based on a signal-to-noise ratio of 3. Although the invention has been described with reference to these preferred embodiments, other embodiments can achieve the same results. Variations and modifications of the present invention will be obvious to those skilled in the art and it is intended to cover in the appended claims all such modifications and equivalents.

What is claimed is:

1. A batch injection analysis apparatus for measuring analyte sample concentration comprising:
    vessel means;
    single batch electrolyte means confined within said vessel means;
    means for serially introducing into said vessel means, for dilution in said single batch electrolyte means, multiple analyte samples to be analyzed, the volume of each said analyte sample having a proportional ratio to the volume of said single batch electrolyte means within the range of 1/20,000 to 1/50,000;
    planar detection means in said vessel means for sensing said analyte samples to be analyzed; and
    means for analyzing said analyte samples.

2. The invention of claim 1 wherein said vessel means further comprises stirrer means.

3. The invention of claim 2 wherein said stirrer means comprises magnetic stirrer means.

4. The invention of claim 1 wherein said electrolyte means is inert relative to said analyte sample.

5. The invention of claim 1 wherein said electrolyte means comprises at least one solution selected from the group consisting of potassium chloride, a phosphate buffer and sodium hydroxide, potassium dihydrogen phosphate and sodium nitrate, and $CH_3COONa$, $CH_3COOH$, NaCl, and 1,2 diaminocyclohexane-N,N,N',N', tetraacetic acid.

6. The invention of claim 5 wherein said electrolyte means comprises $CH_3COONa$, $CH_3COOH$, NaCl; 1,2 diaminocyclohexane-N,N,N',N', tetraacetic acid; and aluminum sulfate.

7. The invention of claim 1 wherein said means for introducing analyte samples into said vessel means comprises injection means.

8. The invention of claim 7 wherein said injection means comprises pipette means.

9. The invention of claim 1 wherein said detector means comprises electrode means.

10. The invention of claim 9 wherein said electrode means comprises carbon paste.

11. The invention of claim 10 wherein said carbon paste electrode means further comprises at least one member selected from the group consisting of glucose oxidase and ruthenium dioxide.

12. The invention of claim 9 wherein said electrode means comprises pH electrode means.

13. The invention of claim 9 wherein said electrode means comprises ion-selective electrode means.

14. The invention of claim 13 wherein said ion-selective electrode means comprises a member selected from the group consisting of chloride electrode means and fluoride electrode means.

15. The invention of claim 1 wherein said means for analyzing said analyte samples comprises amperometric means.

16. The invention of claim 1 wherein said means for analyzing said analyte samples comprises potentiometric means.

17. The invention of claim 1 wherein said means for introducing samples to be analyzed and said means for sensing said samples are positioned at a distance from each other less than 2 mm.

18. The invention of claim 1 wherein said means for introducing samples to be analyzed and said means for sensing said samples are positioned at a distance from each other within 2 to 10 mm.

19. The invention of claim 1 wherein said means for introducing samples to be analyzed and said means for sensing said samples are positioned at a distance from each other greater than 10 mm.

20. A batch injection analytical method for measuring analyte sample concentration comprising the steps of:
    a) providing a vessel;
    b) confining a single batch of an electrolyte within the vessel;
    c) serially introducing into the vessel, for dilution in the single batch of electrolyte, multiple samples to be analyzed, such that the ratio of each sample volume to the single batch of electrolyte volume is within the range of 1/20,000 to 1/50,000;
    d) sensing the samples to be analyzed; and
    e) analyzing the samples.

21. The method of claim 20 further comprising the step of stirring the samples.

22. The method of claim 20 wherein the step of confining an electrolyte within the vessel comprises the step of confining an inert electrolyte within the vessel.

23. The method of claim 22 wherein the step of confining an inert electrolyte within the vessel comprises the step of confining at least one solution selected from the group consisting of potassium chloride; a phosphate buffer and sodium hydroxide; potassium dihydrogen phosphate and sodium nitrate; and $CH_3COONa$, $CH_3COOH$, NaCl, and 1,2 diaminocyclohexane-N,N,N',N', tetraacetic acid.

24. The method of claim 23 wherein the step of confining an inert electrolyte within the vessel comprises the step of confining $CH_3COONa$, $CH_3COOH$, NaCl; 1,2 diaminocyclohexane-N,N,N',N', tetraacetic acid; and aluminum sulfate.

25. The method of claim 20 wherein the step of introducing samples to be analyzed into the vessel comprises the step of injecting analyte samples into the vessel.

26. The method of claim 25 wherein the step of injecting samples into the vessel further comprises pipetting analyte samples into the vessel.

27. The method of claim 20 wherein the step of sensing the analyte samples to be analyzed comprises the step of detecting the samples with an electrode.

28. The method of claim 27 wherein the step of detecting the analyte samples with an electrode comprises providing a carbon paste electrode.

29. The method of claim 28 wherein the step of providing a carbon paste electrode further comprises the step of providing glucose oxidase on the electrode.

30. The method of claim 28 wherein the step of providing a carbon paste electrode further comprises the step of providing ruthenium dioxide on the electrode.

31. The method of claim 27 wherein the step of detecting the samples with an electrode comprises providing a pH electrode.

32. The method of claim 27 wherein the step of detecting the samples with an electrode comprises providing an ion-selective electrode.

33. The method of claim 32 wherein the step of providing ion-selective electrodes comprises providing a member selected from the group consisting of chloride electrodes and fluoride electrodes.

34. The method of claim 20 wherein the step of analyzing the analyte samples comprises measuring amperometric responses of the analyte samples.

35. The method of claim 20 wherein the step of analyzing the analyte samples comprises measuring potentiometric responses of the analyte samples.

36. The method of claim 20 further comprising the step of positioning the means for introducing samples and the sensing means at a distance under 2 mm from each other.

37. The method of claim 20 further comprising the step of positioning the means for introducing samples and the sensing means at a distance within 2 mm to 10 mm from each other.

38. The method of claim 20 further comprising the step of positioning the means for introducing samples and the sensing means at a distance greater than 10 mm from each other.

* * * * *